United States Patent
Hlavka et al.

(10) Patent No.: US 7,214,669 B2
(45) Date of Patent: May 8, 2007

(54) TETRACYCLINE DERIVATIVES AND METHODS OF USE THEREOF

(75) Inventors: Joseph J. Hlavka, Tuxedo Park, NY (US); Richard J. Ablin, Ringwood, NJ (US)

(73) Assignee: Tetragenex Pharmaceuticals, Inc., Park Ridge, NJ (US)

(*) Notice: Subject to any disclaimer, the term of this patent is extended or adjusted under 35 U.S.C. 154(b) by 0 days.

(21) Appl. No.: 10/264,454

(22) Filed: Oct. 4, 2002

(65) Prior Publication Data

US 2004/0067912 A1 Apr. 8, 2004
US 2005/0245491 A9 Nov. 3, 2005

Related U.S. Application Data

(60) Provisional application No. 60/327,502, filed on Oct. 5, 2001.

(51) Int. Cl.
*A61K 31/65* (2006.01)
*C07C 237/26* (2006.01)

(52) U.S. Cl. .............. 514/152; 552/203; 552/205; 552/206

(58) Field of Classification Search ............. 552/205, 552/203, 204, 206; 514/152, 150, 151
See application file for complete search history.

(56) References Cited

U.S. PATENT DOCUMENTS

| | | | |
|---|---|---|---|
| 3,029,284 A | 4/1962 | Gordon | |
| 3,145,228 A * | 8/1964 | Stephens, Jr. et al. | 552/205 |
| 3,265,732 A | 8/1966 | Miller et al. | |
| 3,338,963 A * | 8/1967 | Boothe et al. | 552/205 |
| 3,345,370 A | 10/1967 | Esse et al. | |
| 3,345,410 A * | 10/1967 | Winterbottom et al. | 552/205 |
| 3,388,162 A * | 6/1968 | Winterbottom et al. | 552/205 |
| 3,502,660 A | 3/1970 | Butler et al. | |
| 3,502,696 A | 3/1970 | Conover | |
| 3,509,184 A | 4/1970 | Conover et al. | |
| 3,515,731 A | 6/1970 | Conover | |
| 3,609,188 A | 9/1971 | Esse et al. | |
| 3,622,627 A | 11/1971 | Blackwood et al. | |
| 3,772,363 A | 11/1973 | Conover et al. | |
| 3,824,285 A | 7/1974 | Blackwood et al. | |
| 3,829,453 A | 8/1974 | Conover et al. | |
| 3,849,493 A | 11/1974 | Conover et al. | |
| 4,666,897 A | 5/1987 | Golub et al. | |
| 4,704,383 A | 11/1987 | McNamara et al. | |
| 4,935,411 A | 6/1990 | McNamara et al. | |
| 4,935,412 A | 6/1990 | McNamara et al. | |
| 5,045,538 A | 9/1991 | Schneider et al. | |
| 5,122,519 A | 6/1992 | Ritter | |
| RE34,656 E | 7/1994 | Golub et al. | |
| 5,494,903 A | 2/1996 | Hlavka et al. | |
| 5,495,030 A | 2/1996 | Sum et al. | |
| 5,532,227 A | 7/1996 | Golub et al. | |
| 5,776,898 A | 7/1998 | Teicher et al. | |
| 6,506,740 B1 * | 1/2003 | Ashley et al. | 514/152 |
| 6,818,634 B2 * | 11/2004 | Nelson et al. | 514/152 |
| 6,894,036 B2 * | 5/2005 | Ashley et al. | 514/152 |

OTHER PUBLICATIONS

Van der Bozert et al., Cancer Res. 48:6686-6690 (1988).*
*The Chemistry of Tetracyclines*, Chapter 6, Marcel Dekker Publishers, NY (1978).
Golub, et al., *J. Periodont. Res.*, 20:12-23 (1985).
Greenwald, et al., *Tetracyclines Suppress Metalloproteinase Activity in Adjuvant Arthritis and, in Combination with Flurbioprofen Ameliorate Bone Damage*, Jouranl of Rheumatology 19:927-938 (1992).
Greenwald, et al., *Treatment of Destructive Arthritic Disorders with MMP Inhibitors*, Annals of the New York Academy of Sciences 732:181-198 (1994).
Kloppenburg, et al., *Minocycline in Active Rheumatoid Arthritis*, Arthritis Rheum 37:629-636 (1994).
Ryan, et al., *Potential of Tetracyclines to Modify Cartilage Breakdown in Osteoarthritis*, Current Opinion in Rheumatology 8:38-247 (1996).
O'Dell, et al., *Treatment of Early Rheumatoid Arthritis with Minocycline or Placebo*, Arthritis Rheum 40:842-848 (1997).
White, et al., *Lancet*, Apr. 29, p. 966 (1989).
DeClerk, et al., *Matrix Metalloproteinases and Their Inhibitors in Tumor Progression*, Annals N.Y. Acad. Sci., 732:222-232 (1994).
Rifkin, et al., *Modulation of Bone Resorption by Tetracyclines*, Annals N.Y. Sci., 732:165-180 (1994).
Maragoudakis, et al., *Evidence that Nitric Oxide is an Endogenous Antiangiogenic Mediator*, Br. J. Pharmacol., 111:894-902 (1994).
Ramamurthy, et al., *CMT/Tenidap Treatment Inhibits Temporomandibular Joint Destruction in Adjuvant Arthritic Rats*, Annals N.Y. Acad. Sci., 732, 427-430 (1994).
Golub et al., Tetracyclines inhibit connective tissue breakdown: new therapeutic implications for an old family of drugs (1991) Crit. Revs. Oral. Biol. Med. 2(3): 297-321.

* cited by examiner

*Primary Examiner*—Sabiha N. Qazi
(74) *Attorney, Agent, or Firm*—Paul Diamond, Esq.

(57) ABSTRACT

A treatment for inhibiting microbial or tumor growth is disclosed, which comprises adding to a subject in need of treatment an effective amount of one or more tetracycline derivatives.

12 Claims, No Drawings

TETRACYCLINE DERIVATIVES AND METHODS OF USE THEREOF

This application claims the benefit of U.S. provisional application Ser. No. 60/327,502 filed Oct. 5, 2001.

FIELD OF INVENTION

The present invention relates to novel tetracycline derivatives, methods for producing the novel derivatives and methods of using these derivatives.

BACKGROUND OF THE INVENTION

The compound tetracycline, exhibits the following general structure

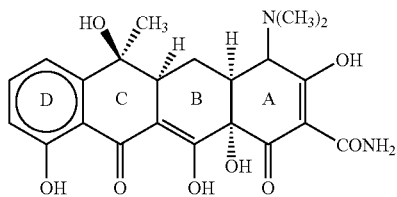

The numbering system of the ring nucleus is as follows:

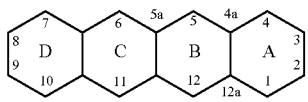

Tetracycline as well as the 5-OH (Terramycin) and 7-Cl (Aureomycin) derivatives exist in nature, and are well known antibiotics. Natural tetracycline may be modified without losing their antibiotic properties, although certain elements of the structure must be retained. The modifications that may and may not be made to the basic tetracycline structure have been reviewed by Mitscher in *The Chemistry of Tetracyclines*, Chapter 6, Marcel Dekker, Publishers, New York (1978). According to Mitscher, the substituents at positions 5–9 of the tetracycline ring system may be modified without the complete loss of antibiotic properties. Changes to the basic ring system or replacement of the substituents at positions 1–4 and 10–12, however, generally lead to synthetic tetracyclines with substantially less or effectively no antimicrobial activity. Some examples of chemically modified non-antimicrobial tetracyclines (hereinafter CMT) are 4-dedimethylaminotetraccyline, 4-dedimethylaminosancycline (6-demethyl-6-deoxy-4-dedimethylaminotetracycline), 4-dedimethylaminominocycline (7-dimethylamino-4-dedimethylaminotetracycline), and 4-dedimethylaminodoxycycline (5-hydroxy-6-deoxy-4-dedimethyaminotetracycline).

Some 4-dedimethylaminotetracycline derivatives are disclosed in U.S. Pat. Nos. 3,029,284 and 5,122,519. They include 6-demethyl-6-deoxy-4-dedimethylaminotetraccyline and 5-hydroxy-6-deoxy-4-dedimethylaminotetracycline with hydrogen and other substituents at C7, and the C9 positions on the D ring. These substitutents include amino, nitro, di (lower alkyl) amino, and mono (lower alkyl) amino or halogen. The 6-demethyl-6-deoxy-4-dedimethylaminotetracycline derivatives and 5-hydroxy-6-deoxy-4-dedimethylaminotetracycline derivatives are said to be useful as antimicrobial agents.

Other 4-dedimethylaminotetracycline derivatives with an oxime group at the C4 position on the A ring are disclosed in U.S. Pat. Nos. 3,622,627 and 3,824,285. These oxime derivatives have hydrogen and halogen as substitutents at the C7 position and include 7-halo-6-demethyl-6-deoxy-4-dedimethylamino-4-oximinotetracycline, and 7-halo-5-hydroxy-6-deoxy-4-dedimethylamino-4-oximinotetracycline.

Alkylamino (NH-alkyl), and alkylhydrazone (N—NH-alkyl) groups have been substituted on the A ring at the C4 position of 4-dedimethylaminotetracycline. These compounds are known for their antimicrobial properties. See U.S. Pat. Nos. 3,345,370, 3,609,188, 3,622,627, 3,502,660, 3,509,184, 3,502,696, 3,515,731, 3,265,732, 5,122,519, 3,849,493, 3,772,363, and 3,829,453.

In addition to their antimicrobial properties, tetracyclines have been described as having a number of other uses. For example, tetracyclines are also known to inhibit the activity of collagen destructive enzymes, such as matrix metalloproteinases (MMP), including collagenases (MMP-1), gelatinase (MMP-2) and stromelysin (MMP-3). Golub et al., *J. Periodont. Res.* 20:12–23 (1985); Golub et al. *Crit. Revs. Oral Biol. Med.* 2:297–322 (1991); U.S. Pat. Nos. 4,666,897; 4,704,383; 4,935,411; 4,935,412. Also, tetracyclines have been known to inhibit wasting and protein degradation in mammalian skeletal muscle, U.S. Pat. No. 5,045,538, and to enhance IL-10 production in mammalian cells.

Furthermore, tetracyclines were reported to enhance bone protein synthesis in U.S. Pat. No. Re. 34,656, and to reduce bone resorption in organ culture in U.S. Pat. No. 4,704,383.

Similarly, U.S. Pat. No. 5,532,227 to Golub et al, discloses that tetracyclines can ameliorate the excessive glycosylation of proteins. In particular, tetracyclines inhibit the excessive collagen cross linking which results from excessive glycosylation of collagen in diabetes.

Tetracyclines are known to inhibit excessive phospholipase $A_2$ activity involved in inflammatory conditions such as psoriasis as disclosed in U.S. Pat. No. 5,532,227. In addition, tetracyclines are also known to inhibit cycloxygenase-2 (COX-2), tumor necrosis factor (TNF), nitric oxide and IL-1 (interleukin-1).

These properties cause the tetracyclines to be useful in treating a number of diseases. For example, there have been a number of suggestions that tetracyclines, including non-antimicrobial tetracyclines, are effective in treating arthritis. See, for example, Greenwald, et al. "Tetracyclines Suppress Metalloproteinase Activity in Adjuvant Arthritis and, in Combination with Flurbioprofen, Ameliorate Bone Damage," *Journal of Rheumatology* 19:927–938 (1992); Greenwald et al., "Treatment of Destructive Arthritic Disorders with MMP Inhibitors; Potential Role of Tetracyclines in Inhibition of Matrix Metalloproteinases: *Therapeutic Potential,*" *Annals of the New York Academy of Sciences* 732: 181–198 (1994); Kloppenburg, et al. "Minocycline in Active Rheumatoid Arthritis," *Arthritis Rheum* 37:629–636 (1994); Ryan et al., "Potential of Tetracycline to Modify Cartilage Breakdown in Osteoarthritis," *Current Opinion in Rheumatology* 8:238–247 (1996); O'Dell et al, "Treatment of Early Rheumatoid Arthritis with Minocycline or Placebo," *Arthritis Rheum* 40:842–848 (1997).

Tetracyclines have also been suggested for use in treating skin diseases. For example, White et al., *Lancet*, April 29, p. 966 (1989) report that the tetracycline minocyline is effective in treating dystrophic epidermolysis bullosa, which is a life-threatening skin condition believed to be related to excess collagenase.

Furthermore, studies have also suggested that tetracyclines and inhibitors of metalloproteinases inhibit tumor progression, DeClerck et al., *Annals N.Y. Acad. Sci.*, 732: 222–232 (1994), bone resorption, Rifkin et al., *Annals N.Y. Acad. Sci.*, 732:165–180 (1994), angiogenesis, Maragoudakis et al., *Br. J. Pharmacol.*, 111:894–902 (1994), and may have anti-inflammatory properties, Ramamurthy et al., *Annals N.Y. Acad. Sci.*, 732, 427–430 (1994).

Based on the foregoing, tetracyclines have been found to be effective in treating numerous diseases and conditions. Therefore, there is a need for new and even more useful derivatives.

DESCRIPTION OF THE PREFERRED EMBODIMENTS

Compounds disclosed herein are derivatives of tetracycline, which exhibit antimicrobial and/or anti-cancer activity.

In a preferred embodiment, the present invention relates to a treatment for inhibiting microbial or tumor growth which comprises adding to a subject in need of said treatment an effective amount of a tetracycline composition or salt thereof, comprising a general formula:

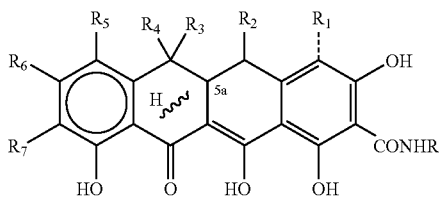

wherein R is selected from $CH_2N(R_aR_b)$ or

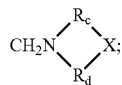

$R_aR_b$ are $C_1$ to $C_6$ alkyl;
$R_c$ and $R_d$ are $(CH_2)_n CHR_e$, n is 0 or 1 and $R_e$ is H, $C_1$ to $C_6$ alkyl, or $NH_2$, and X is NH, S, or $CH_2$;
$R_1$ is H or OH;
$R_2$ is H, OH, =O, or $OCOR_8$, where $R_8$ is $C_1$ to $C_6$ alkyl, or alternatively, $R_2$ is $N(R_9)_2$, where $R_9$ is hydrogen or $C_1$ to $C_6$ lower alkyl, or $R_9$ CO, with the proviso that when $R_2$ is keto or $N(R_9)_2$, then $R_3$ and $R_4$ are H or $CH_3$, and $R_3$ and $R_4$ are not both $CH_3$ or H;
5a hydrogen is α or β;
$R_3$ and $R_4$ are H, $CH_3$ or F, with the proviso that when $R_3$ is $CH_3$, then $R_4$ is H or F, and when $R_4$ is $CH_3$, then $R_3$ is H or F and $R_4$ and $R_5$ are not both F;
$R_5$ and $R_7$ are halogen, H, $NO_2$, $N_3$, $N_2^+$, $C_2H_5OC(S)S$—, CN, $NR_{10}R_{11}$, where $R_{10}$ and $R_{11}$ are H, $C_1$ to $C_{10}$ alkyl, and $R_{12}(CH_2)_nCO$—, where n is 0 to 5 and $R_9$ is H, $NH_2$, mono or disubstituted amino selected from straight, branched or cyclized $C_1$ to $C_{10}$ alkyl groups, with the proviso that $R_{10}$ and $R_{11}$ are not both $R_{12}(CH_2)_nCO$—;
$R_7$, alternatively, is tertiary butyl; and
$R_6$ is halogen, acetylene, $R_{13}$—$C_6H_5$, where $R_{13}$ is $NO_2$, halogen, acetylamino, amino, phenyl, alkyl, or alkoxy.

In a further preferred embodiment, the present invention relates to a treatment for inhibiting microbial or tumor growth which comprises adding to a subject in need of said treatment an effective amount of a tetracycline composition or salt thereof, comprising a general formula:

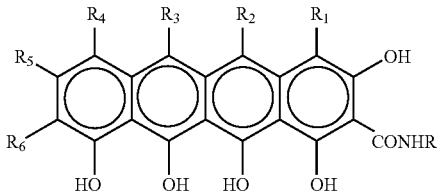

wherein R is selected from $CH_2N(R_aR_b)$ or

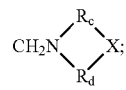

where $R_aR_b$ are $C_1$ to $C_6$ alkyl;
$R_c$ and $R_d$ are $(CH_2)_n CHR_e$, n is 0 or 1 and $R_e$ is H, $C_1$ to $C_6$ alkyl, or $NH_2$, and X is NH, S, or $CH_2$;
$R_1$ is H or OH;
$R_2$ is H or OH;
$R_3$ is H or $CH_3$;
$R_4$ and $R_6$ are halogen, H, $NO_2$, $N_3$, $N_2^+$, $C_2H_5OC(S)S$—, CN, $NR_7R_8$, where $R_7$ and $R_8$ are H, $C_1$ to $C_{10}$ alkyl, and $R_9(CH_2)_nCO$—, where n is 0 to 5 and $R_9$ is H, $NH_2$, mono or disubstituted amino selected from straight, branched or cyclic $C_1$–$C_{10}$ alkyl, with the proviso that $R_7$ and $R_8$ are not both $R_9(CH_2)_nCO$—; and
$R_6$ is H or halogen, acetylene, $R_{10}$—$C_6H_5$, where $R_{10}$ is $NO_2$, halogen, acetylamino, amino, phenyl, alkyl, or alkoxy.

In a further preferred embodiment, the present invention relates to a treatment for inhibiting microbial or tumor growth which comprises adding to a subject in need of said treatment an effective amount of a tetracycline composition or salt thereof, comprising a general formula:

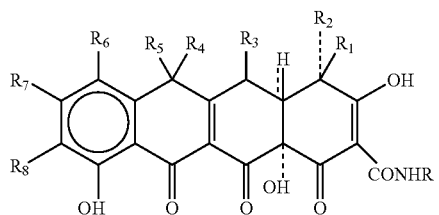

wherein R is selected from $CH_2N(R_aR_b)$ or

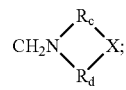

where $R_aR_b$ are $C_1$–$C_6$ alkyl;
$R_c$ and $R_d$ are $(CH_2)_n CHR_e$, n is 0 or 1 and $R_e$ is H, $C_1$ to $C_6$ alkyl, or $NH_2$, and X is NH, S, or $CH_2$;
$R_1$ and $R_2$ are H or $N(R_9)_2$, where $R_9$ is H or $C_1$ to $C_6$ alkyl with the proviso that $R_1$ and $R_2$ are not both $N(R_9)_2$, $R_1$ and $R_2$ are also $N(R_{10})_3$ I, where $R_{10}$ is $C_1$ to $C_6$ alkyl, with the proviso that $R_1$ and $R_1$ are not both $N(R_{10})_3$ I;

$R_3$ is H;

$R_4$ and $R_5$ are H, $CH_3$ or F, with the proviso that when $R_4$ is $CH_3$, then $R_5$ is H or F, and when $R_5$ is $CH_3$, then $R_4$ is H or F, and $R_4$ and $R_5$ are not both F;

$R_6$ and $R_8$ are halogen, H, $NO_2$, $N_3$, $N_2^+$, $C_2H_5OC(S)S-$, CN, $NR_{11}R_{12}$, where $R_{11}$ and $R_{12}$ are H, $C_1$ to $C_{10}$ alkyl, and $R_{13}(CH_2)_nCO-$, where n is 0 to 5 and $R_{13}$ is H, $NH_2$, mono or disubstituted amino selected from straight, branched or cyclized $C_1$–$C_{10}$ alkyl groups, with the proviso that $R_{10}$ and $R_{11}$ are not both $R_{12}$ $(CH_2)_nCO-$; and $R_8$ can also be tertiary butyl and $R_7$ is H or halogen.

In an additional preferred embodiment, the present invention relates to a treatment for inhibiting microbial or tumor growth which comprises adding to a subject in need of said treatment an effective amount of a tetracycline composition or salt thereof, comprising a general formula:

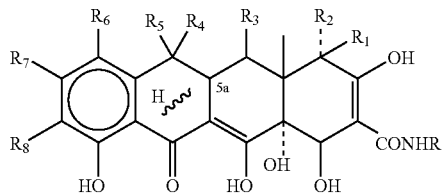

wherein R is selected from $CH_2N(R_aR_b)$ or

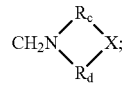

$R_a$ $R_b$ are $C_1$–$C_6$;

$R_c$ and $R_d$ are $(CH_2)n$ $CHR_e$, n is 0 or 1, $R_e$ is H, alkyl ($C_1$ to $C_6$), $NH_2$, and X is NH, S, or $CH_2$;

$R_1$ and $R_2$ are H or $N(R_9)_2$ where $R_9$ is hydrogen or lower alkyl ($C_1$ to $C_6$), with the proviso that $R_1$ and $R_2$ can not both be $N(R_9)_2$.

$R_3$ is H, OH, =O, $OCOR_{10}$, where $R_{10}$ is $C_1$ to $C_6$, or alternatively, $R_3$ is $N(R_9)_2$ where $R_9$ is hydrogen or $C_1$ to $C_6$, with the proviso that when $R_{23}$ is =O or $N(R_9)_2$, then $R_4$ and $R_5$ are H or $CH_3$ and $R_4$ and $R_5$ are not both $CH_3$ or H;

5a hydrogen is α or β;

$R_4$ and $R_5$ are H, $CH_3$ or F, with the proviso that when $R_4$ is $CH_3$, then $R_5$ is H or F, and when $R_5$ is $CH_3$ then $R_4$ is H or F and $R_4$ and $R_5$ are not both F;

$R_6$ and $R_8$ are halogen, H, $NO_2$, $N_3$, $N_2^+$, $C_2H_5OC(S)S-$, CN, $NR_{10}R_{11}$, where $R_{10}$ and $R_{11}$ are H, alkyl ($C_1$ to $C_{10}$), and $R_{12}$ $(CH_2)_nCO-$, where n is 0 to 5 and $R_{12}$ is H, $NH_2$, mono or disubstituted amino selected from straight, branched or cyclized $C_1$ to $C_{10}$ groups, with the proviso that $R_{10}$ and $R_{11}$ are both $R_{12}$ $(CH_2)_nCO-$, or, alternatively, $R_8$ is tertiary butyl;

$R_7$ is H or halogen, acetylene, $R_{12}$—$C_6H_5$, where $R_{12}$ is $NO_2$, halogen, acetylamino, amino, phenyl, alkyl, or alkoxy.

In a further preferred embodiment, the present invention relates to a treatment for inhibiting microbial or tumor growth which comprises adding to a subject in need of said treatment an effective amount of a tetracycline composition or salt thereof, comprising a general formula:

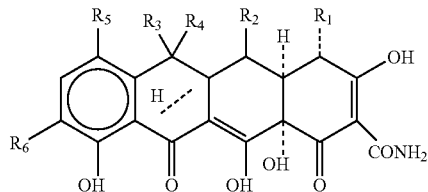

wherein $R_1$ is H or $N(CH_3)_2$; $R_2$ is H, $CH_3$ or $OCOCH_3$; $R_3$ is H or $CH_3$; $R_4$ is H; $R_5$ is H, $N(CH_3)_2$, $NH_2$, $N(C_4H_9)_2$, $N(C_6H_{13})_2$, $N(3,3$-dimethylbutyl$)_2$, $N_3$, $N_2^+$, $NO_2$, $NHCOCH_3$, NH(n-propyl)$_2$, NH-isobutyl, NH-isobutylmethyl, NH(cyclobutyl), NH(cyclobutyl methyl); and $R_6$ is H, $NO_2$, $NH_2$, $(CH_3)_2$ CHNH, $N_3$, $NHCOCH_3$, $N_2^+$, $N_3$ or $(CH_3)_3C$.

In a further preferred embodiment, the present invention relates to a treatment for inhibiting microbial or tumor growth which comprises adding to a subject in need of said treatment an effective amount of a tetracycline composition or salt thereof, comprising a general formula:

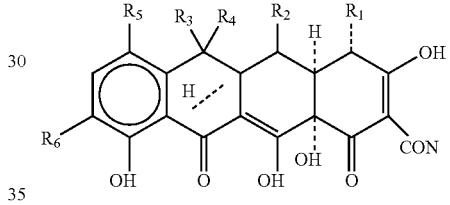

wherein $R_1$ is H or $N(CH_3)_2$; $R_2$ is H, OH or $OCOCH_3$; $R_3$ is H or $CH_3$; $R_4$ is H; $R_5$ is H, $N(CH_3)_2$; $N(C_4H_9)_2$, $N(C_6H_{13})_2$, $N(3,3$-dimethylbutyl$)_2$, $N_3$, $N_2^+$, $NO_2$, $NHCOCH_3$, NH(n-propyl)$_2$, NH-isobutyl, NH-isobutylmethyl, N($CH_3CO$)(isobutyl), NH(cyclobutyl), NH(cyclobutyl methyl), or $NH_2$; and $R_6$ is H, $NO_2$, $NH_2$, $(CH_3)_2$ CHNH, $N_3$, $NHCOCH_3$, $N_2^+$, or $(CH_3)_3C$.

The following examples describe the preparation of various substances in accordance with the present invention.

HPLC analyses were performed on Waters reverse phase $C_{18}$-symmetry columns using water (containing 0.1% TFA) and acetonitrile as eluents Analytical LC/MS runs were performed on a Hewlett Packard Series 1100 liquid chromatographer equipped with a series 1100 MSD detector, with ES ionization mode and UV detection at 270 nm, using a 4.6×100 mm column with a flow rate of 0.4 mL/min. Preparative HPLC was performed on a Gilson serial HPLC with UV detection at 270 nm, using a 19×150 mm column and a flow rate of 15 mL/min $^1$H NMR were recorded on a Bruker 300 MHz spectrometer in deuterated methanol.

9-Nitro-doxycycline sulfate

To a stirred solution of doxycycline hydrochloride (1 g, 2.08 mmol) in 30 mL of concentrated sulfuric acid at 0° C. was added potassium nitrate (252 mg, 2.49 mmol). The resulting mixture was stirred for 20 min at 0° C., then poured into 1.2 L cold ether with stirring. The solid which precipitated was filtered out, washed with cold ether and dried under vacuum, and 1.22 g of cream colored product was obtained. If needed, the product was purified by dissolving in methanol, filtering and pouring the filtrate into ether. The solid which separated was filtered out and dried.

9-Amino-doxycycline sulfate To a stirred solution of 9-nitro-doxycycline sulfate (1 g, 1.7 mmol) in 35 mL of ethylene glycol monomethyl ether and 5 mL of methanol was added 700 mg of 10% Pd/C. The reaction mixture was hydrogenated at atmospheric pressure for 6 hrs. The catalyst was filtered off through celite washing with methanol. The filtrate was concentrated, then added dropwise to 800 mL cold ether with stirring. The solid that separated was filtered out, washed with cold ether and dried under vacuum, and 843 mg of cream colored product was obtained.

9-Isopropylamino-doxycycline sulfate

To a stirred solution of 9-amino-doxycycline sulfate (100 mg, 0.18 mmol) on 10 mL of ethylene glycol monomethyl ether was added 0.05 ml of concentrated sulfuric acid, 0.5 mL acetone and 100 mg of 10% Pd/C. The resulting mixture was hydrogenated at atmospheric pressure for 1 h 15 min, then the catalyst was filtered through celite, washing with methanol. The filtrate was concentrated, then poured into 150 mL of cold ether with stirring. The solid that separated was filtered out, washed with cold ether and dried under vacuum, and 109 mg of cream colored product was obtained. The product was purified by dissolving in methanol, filtering and pouring the filtrate into ether. The solid which formed was filtered out and dried.

9-Acetamido-doxycycline sulfate

To a stirred solution of 9-amino-doxycycline sulfate (72 mg, 0.13 mmol) in 1.5 mL of 1,3-dimethyl-2-imidazolidinone were added 70 mg sodium bicarbonate followed by 0.05 mL of acetyl chloride. The mixture was stirred at room temperature for 1 hour and then filtered. The filtrate was concentrated and poured into 100 ml cold ether with stirring. The solid that separated was filtered out and dried under vacuum, and 92 mg was obtained.

9-Diazonium-doxycycline sulfate hydrochloride

To a stirred solution of 9-amino-doxycycline sulfate (300 mg, 0.54 mmol) in 9 mL of 0.1N hydrochloric acid in methanol cooled in an ice bath was added 0.3 mL of n-butyl nitrite. The solution was stirred at 0° C. for 30 minutes then poured into 300 mL of cold ether with stirring. The solid that separated was filtered out and dried under vacuum, and 256 mg of an orange-brown product was obtained.

9-Azido-doxycycline sulfate

To a stirred solution of 9-diazonium-doxycycline sulfate hydrochloride (80 mg, 0.14 mmol) in 4.5 mL of 0.1N hydrochloric acid in methanol was added 10 mg of sodium azide. The solution was stirred at room temperature for 2 hours, then poured into 100 mL of cold ether with stirring. The solid that separated was filtered out and dried under vacuum, and 43 mg of product was obtained.

9-(4-flurophenyl)-doxycycline

To a stirred solution of 9-diazonium-doxycycline sulfate hydrochloride (358 mg, 0.59 mmol) and 4-flurophenyl boronic acid (107 mg, 0.76 mmol) in 4 mL of methanol was added 18 mg of palladium(II)acetate and the resulting mixture was stirred at room temperature for 16 hours. The catalyst was filtered off and the residue was concentrated and purified by preparative HPLC. The collected fractions from HPLC were concentrated and poured into 20 ml of cold ether. The solid that was separated was filtered out and dried under vacuum, and 32 mg of product was obtained.

7-[1,2-bis(carbobenzyloxy)hydrazino]-doxycycline

To a stirred solution of doxycycline hydrochloride (300 mg, 0.62 mmol) in 2.5 ml of THF and 3.2 mL of methanesulfonic acid at 0° C. was added 230 mg of dibenzyazodicarboxylate. The resulting mixture was stirred at 0° C. for 2 hours, then poured into 400 mL of cold ether. The solid that separated was filtered out and dried under vacuum, and 479 mg of an off-white product was obtained.

7-Amino-doxycycline

To a solution of 7-[1,2-bis(carbobenzyloxy)hydrazino]-doxycycline (478 mg) in 30 mL of ethylene glycol monomethyl ether was added 200 mg of 10% Pd/C and the resulting mixture was hydrogenated for 3 hours at room temperature. The catalyst was filtered through celite washing with methanol and the filtrate was concentrated and poured into 500 mL cold ether. The solid that separated was filtered out and dried under vacuum, and 268 mg of product was obtained.

7-Dimethylamino-doxycycline sulfate

To a solution of 7-amino-doxycycline (100 mg) in 8 mL of ethylene glycol monomethyl ether were added 1 mL of a 37% aqueous formaldehyde solution, 0.05 mL of concentrated sulfuric acid and 100 mg of 10% Pd/C. The resulting mixture was hydrogenated at atmospheric pressure for 6 hours, then the catalyst was filtered through celite, washing with methanol. The residue was concentrated and poured into 100 ml cold ether with stirring. The solid that separated was filtered out with difficulty, being very gluey. The solid was immediately redissolved in methanol and poured into 100 ml cold ether with stirring. The solid that separated was filtered out and dried under vacuum, and 89 mg of product was obtained.

7-Dipropyl-doxycycline sulfate

To a solution of 7-amino-doxycycline (90 mg) in 8 ML of ethylene glycol monomethyl ether were added 0.5 mL of propionaldehyde, 0.05 mL of concentrated sulfuric acid and 80 mg of 10% Pd/C. The resulting mixture was hydrogenated at atmospheric pressure for 5 hours, then the catalyst was filtered through celite, washing with methanol. The residue was concentrated and poured into 100 ml cold ether with stirring. The solid that separated was filtered out and dried under vacuum, and 415 mg of product was obtained.

7-Dibutylamino-doxycycline sulfate

To a solution of 7-amino-doxycycline (100 mg, 0.2 mmol) in 6 mL of ethylene glycol monomethyl ether were added 0.6 mL of butyraldehyde, 0.05 mL of concentrated sulfuric acid and 100 mg of 10% Pd/C. The resulting mixture was hydrogenated at atmospheric pressure for 4 hours, then the catalyst was filtered through celite, washing with methanol. The residue was concentrated and poured into 100 ml cold ether with stirring. The solid that separated was filtered out and dried under vacuum, and 103 mg of product was obtained.

7-Di(3,3-dimethyl)butylamino-doxycycline sulfate

To a solution of 7-amino-doxycycline (100 mg, 0.2 mmol) in 6 mL of ethylene glycol monomethyl ether were added 0.5 mL of 3,3-dimethyl butyraldehyde, 0.05 mL of concentrated sulfuric acid and 100 mg of 10% Pd/C. The resulting mixture was hydrogenated at atmospheric pressure for 4 hrs, then the catalyst was filtered through celite, washing with methanol. The residue was concentrated and poured into 100 ml cold ether with stirring. The solid that separated was filtered out and dried under vacuum, and 122 mg of product was obtained.

7-Dihexylamino-doxycycline sulfate

To a solution of 7-amino-doxycycline (100 mg, 0.2 mmol) in 6 mL of ethylene glycol monomethyl ether were added 0.6 mL of hexanal, 0.05 mL of concentrated sulfuric acid and 100 mg of 10% Pd/C. The resulting mixture was hydrogenated at atmospheric pressure for 4 hours, then the catalyst was filtered through celite, washing with methanol. The residue was concentrated and poured into 100 ml cold ether with stirring. The solid that separated was filtered out and dried under vacuum, and 129 mg of product was obtained.

7-Isopropylamino-doxycycline sulfate

To a solution of 7-amino-doxycycline (90 mg, 0.2 mmol) in 8 mL of ethylene glycol monomethyl ether were added 0.5 mL of isobutyraldehyde, 0.05 mL of concentrated sulfuric acid and 90 mg of 10% Pd/C. The resulting mixture was hydrogenated at atmospheric pressure for 6 hours, then the catalyst was filtered through celite, washing with methanol. The residue was concentrated and poured into 100 ml cold ether with stirring. The solid that separated was filtered out and dried under vacuum, and 142 mg of product was obtained.

7-Methyl-7-isopropylamino-doxycycline sulfate

To a solution of 7-isopropylamino-doxycycline (60 mg) in 4 mL of ethylene glycol monomethyl ether were added 0.4 mL of a 37% aqueous solution of formaldehyde, 0.05 mL of concentrated sulfuric acid and 50 mg of 10% Pd/C. The resulting mixture was hydrogenated at atmospheric pressure for 2 hours, then the catalyst was filtered through celite, washing with methanol. The residue was concentrated and poured into 80 ml cold ether with stirring. The solid that separated was filtered out and dried under vacuum, and 52 mg of product was obtained.

7-Cyclobutylamino-doxycycline sulfate

To a solution of 7-amino-doxycycline (80 mg) in 7 mL of ethylene glycol monomethyl ether were added 0.3 mL of cyclobutanone, 0.04 mL of concentrated sulfuric acid and 60 mg of 10% Pd/C. The resulting mixture was hydrogenated at atmospheric pressure for 24 hours, then the catalyst was filtered through celite, washing with methanol. The residue was concentrated and poured into 100 ml cold ether with stirring. The solid that separated was filtered out and dried under vacuum, and 85 mg of product was obtained.

7-Methyl-7-cyclobutylamino-doxycycline sulfate

To a solution of 7-cyclobutylamino-doxycycline (40 mg) in 3.5 mL of ethylene glycol monomethyl ether were added 0.3 mL of a 37% aqueous solution of formaldehyde, 0.03 mL of concentrated sulfuric acid and 40 mg of 10% Pd/C. The resulting mixture was hydrogenated at atmospheric pressure for 6 hrs, then the catalyst was filtered through celite, washing with methanol. The residue was concentrated and poured into 80 ml cold ether with stirring. The solid that separated was filtered out and dried under vacuum, and 35 mg of product was obtained.

7-Acetamido-doxycycline sulfate

To a stirred solution of 7-amino-doxycycline (200 mg) in 3 mL of 1,3-dimethyl-2-imidazolidinone were added 200 mg sodium bicarbonate followed by 0.09 mL of acetyl chloride. The mixture was stirred at room temperature for 1 hr and then filtered. The filtrate was concentrated and poured into 200 ml cold ether with stirring. The product which precipitated was filtered out and dried under vacuum. Obtained 202 mg of product.

7-Acetamido-7-isopropyl-doxycycline sulfate

To a stirred solution of 7-isobutylamino-doxycycline (60 mg) in 1.5 mL of 1,3-dimethyl-2-imidazolidinone were added 60 mg sodium bicarbonate followed by 0.05 mL of acetyl chloride. The mixture as stirred at room temperature for 1 hr 30 min and then filtered. The filtrate was concentrated and poured into 80 ml cold ether with stirring. The product which precipitated was filtered out and dried under vacuum.

7-Diazonium-doxycycline hydrochloride or tetrafluoroborate

To a stirred solution of 7-amino-doxycycline (200 mg, 0.4 mmol) in 4 mL of 0.1N hydrochloric acid in methanol cooled in an ice bath was added 0.2 mL of n-butyl nitrite. The solution was stirred at 0° C. for 30 minutes, then poured into 200 mL of cold ether with stirring. The solid that separated was filtered out and dried under vacuum, and 173 mg of product was obtained. The diazonium tetrafluoroborate salt was prepared by using tetrafluoroboric acid (54% solution in ether) instead of hydrochloric acid.

7-Azido-doxycycline

To a stirred solution of 7-diazonium-doxycycline hydrochloride (80 mg, 0.14 mmol) in 4.5 mL of 0.1N hydrochloric acid in methanol cooled on an ice bath was added 12 mg of sodium azide. The solution was stirred at 0° C. for 2 hours, then poured into 100 mL of cold ether with stirring. The solid that separated was filtered out and dried under vacuum, and 43 mg of product was obtained.

7-Amino-9-nitro-doxycycline sulfate

To a stirred solution of 7-amino-doxycycline (220 g, 0.44 mmol) in 4 mL of concentrated sulfuric acid at 0° C. was added potassium nitrate (52 mg, 0.51 mmol). The resulting mixture was stirred for 15 minutes at 0° C., then poured into 300 mL cold ether with stirring. The solid that separated was filtered out, washed with cold ether and dried under vacuum. The product was redissolved in methanol, filtered and the filtrate was poured into ether. The solid that separated was filtered out and dried under vacuum, and 222 g of product was obtained.

7-Dimethylamino-9-nitro-doxycycline sulfate

To a stirred solution of 7-dimethylamino-doxycycline (40 g, 0.07 mmol) in 1.5 mL of concentrated sulfuric acid at 0° C. was added potassium nitrate (12 mg, 0.12 mmol). The resulting mixture was stirred for 30 min at 0° C., then poured into 60 mL cold ether with stirring. The solid that separated was filtered out, washed with cold ether and dried under vacuum. LC/MS shows mostly one product containing two nitro groups (possibly a nitrate ester of the desired product).

7-Dimethylamino-9-diazonium-doxycycline sulfate hydrochloride

To a stirred solution of 7-dimethylamino-9-amino-doxycycline (50 mg) in 1.5 mL of 0.1N hydrochloric acid in methanol cooled in an ice bath was added 0.05 mL of a n-butyl nitrite. The solution was stirred at 0° C. for 30 minutes, then poured into 80 mL of cold ether with stirring. The solid that separated was filtered out and dried under vacuum, and 38 mg of product was obtained.

7-Acetamido-9-nitro-doxycycline sulfate

To a stirred solution of 7-acetamino-doxycycline (60 g, 0.095 mmol) in 2 mL of concentrated sulfuric acid at 0° C. was added potassium nitrate (11 mg, 0.11 mmol). The resulting mixture was stirred for 5 minutes at 0° C., then poured into 80 mL cold ether with stirring. The solid that separated was filtered out, washed with cold ether and dried under vacuum.

7-Acetamido-9-amino-doxycycline sulfate

To a stirred solution of 7-acetamido-9-nitro-doxycycline sulfate (77 mg, 0.12 mmol) in 7 mL of ethylene glycol monomethyl ether was added 60 mg of 10% Pd/C. The reaction mixture was hydrogenated at atmospheric pressure for 7 hours. The catalyst was filtered off through celite washing with methanol. The filtrate was concentrated, then added dropwise to 100 mL cold ether with stirring. The solid that separated was filtered out, washed with cold ether and dried under vacuum, and 62 mg of product was obtained.

7-Acetamido-9-diazonium-doxycycline sulfate hydrochloride

To a stirred solution of 7-acetamido-9-amino-doxycycline (100 mg) in 3 mL of 0.1N hydrochloric acid in methanol cooled in an ice bath was added 0.1 mL of n-butyl nitrite. The solution was stirred at 0° C. for 30 minutes, then poured into 100 mL of cold ether with stirring. The solid that separated was filtered out and dried under vacuum, and 92 mg of product was obtained.

7-Acetamido-9-azido-doxycycline sulfate

To a stirred solution of 7-acetamido-9-diazonium-doxycycline (112 mg, 0.19 mmol) in 6 mL of 0.1N hydrochloric acid in methanol cooled in an ice bath was added 14 mg (0.21 mmol) of sodium azide. The solution was stirred at 0° C. for 35 minutes, then poured into 150 mL of cold ether with stirring. The solid that separated was filtered out and dried under vacuum, and 94 mg of product was obtained.

Doxycycline Methiodide

Doxycycline free base (315 mg) was dissolved in 2 mL of methanol and 10 mL of THF, then 1 mL of methyl iodide was added. The reaction mixture was kept for 5 days; no crystallization of the product occurred. The reaction mixture was concentrated and poured into 300 mL of cold ether with stirring. The product that separated was filtered out and dried under vacuum, and 269 mg was obtained; LC/MS shows pure product.

5-Acetoxy-doxycycline

A solution of doxycycline (100 mg) in 3 mL of a 30% HBr in acetic acid solution was stirred at room temperature for 3.5 days; the reaction mixture was then poured into 100 mL of cold ether with stirring and the product that separated was filtered out. LC/MS showed incomplete conversion of starting material, so the product (86 mg) was resubjected to the reaction conditions for 9 hrs, and then isolated in the same way.

9-tert-butyl-doxycycline

A solution of doxycycline (100 mg) in 2 mL of tert-butanol and 3 mL of methanesulfonic acid was stirred at room temperature for 18 hours, then poured into 100 mL of cold water and extracted with n-butanol. The organic extracts were basified with a 1N sodium hydroxide solution and the pH was quickly adjusted to 6.5–7 with concentrated hydrochloric acid. A solid precipitated which was filtered out, then dissolved in methanol, concentrated and added dropwise to 30 mL of an ether/PET ether cold solution with stirring. The solid that separated was filter out and dried under vacuum.

9-tert-butyl-7-nitro-doxycycline

A solution of doxycycline hydrochloride (2 g) in 10 mL of tert-butanol and 30 mL of methanesulfonic acid was stirred at room temperature for 3 hours, then 500 mg of potassium nitrate was added and the resulting mixture stirred for an additional hour. The reaction mixture was poured in 100 ml cold solution of water containing 23 g of sodium hydroxide; more dilute NaOH solution was added dropwise until the reaction mixture became basic. The pH was quickly adjusted to 6.5–7 with concentrated hydrochloric acid. The gluey dark solid that separated was filtered out. The aqueous filtrate was extracted once with n-butanol to recover more product. The crude product was dissolved in the minimum amount of methanol and purified by HPLC. The combined fractions from HPLC were concentrated to dryness, dissolved in methanol and added dropwise to 50 mL of a 3:1 mixture of ether/PET ether. The solid that separated was filtered out, and 788 mg of pale yellow product was obtained.

9-tert-butyl-7-amino-doxycycline

To a solution of 9-tert-butyl-7-doxycycline (500 mg) in 25 mL of ethylene glycol monomethyl ether was added 350 mg of 10% Pd/C and the resulting mixture was hydrogenated at atmospheric pressure for 17 hours. The catalyst was filtered through celite, washing with methanol. The residue was concentrated, dissolved in THF and added dropwise to a cold 1:1 solution of ether/PET ether with stirring. The product that precipitated was filtered out and dried under vacuum, and 452 mg of product was obtained.

9-tert-butyl-7-diazonium-doxycycline

To a stirred solution of 9-tert-butyl-7-amino-doxycycline (93 mg, 0.18 mmol) in 2.5 mL of 0.1N hydrochloric acid in methanol cooled in an ice bath was added 0.1 mL of n-butyl nitrite. The solution was stirred at 0° C. for 30 minutes, and then half was poured into 30 mL of a 3:1 cold mixture of ether/PET ether with stirring. The product stuck to the bottom of the beaker as a gum. It was redissolved in methanol and concentrated, the residue was poured into 20 mL of cold ether and the solid that separated was filtered out immediately and dried under vacuum; 42 mg of product was obtained. The other half of the reaction mixture was used directly for the 9-tert-butyl material below.

9-tert-butyl-7-azido-doxycycline

To a stirred solution of 9-tert-butyl-7-diazonium-doxycycline reaction mixture (1.5 mL) at 0° C. were added 8 mg (0.12 mmol) of sodium azide. The solution was stirred for 3 hours while allowed to warm to room temperature. After concentration of the reaction mixture, the residue was poured into a cold 3:1 mixture of ether/PET ether with stirring. No solid separated, so the solution was concentrated to dryness to obtain 35 mg of product.

9-tert-butyl-7-dimethylamino-doxycycline

To a stirred reaction mixture from 9-tert-butyl-7-amino-doxycycline containing 167 mg of 9-tert-butyl-7-amino-doxycycline in 10 mL of ethylene glycol monomethyl ether and 115 mg of 10% Pd/C was added 1.2 ml of a 37% aqueous solution of formaldehyde. The resulting mixture was hydrogenated for 3.5 hours at atmospheric pressure, then the catalyst was filtered through celite washing with methanol. The filtrate was concentrated and the residue was poured into 10 mL of cold ether with stirring. The product that separated was filtered out and dried under vacuum. LC/MS showed the expected product, but was contaminated by baseline impurity.

9-tert-butyl-7-acetamido-doxycycline

To a stirred solution of 9-tert-butyl-7-amino-doxycycline (100 mg) in 2 mL of 1,3-dimethyl-2-imidazolidinone were added 100 mg of sodium bicarbonate followed by 0.07 mL of acetyl chloride. The mixture was stirred at room temperature for 1.5 hours and then filtered. The filtrate was concentrated and poured into 100 mL of cold ether with stirring. The product that separated was filtered out. The crude product was redissolved in methanol, filtered and added dropwise to a cold 3:1 mixture of ether/PET ether with stirring. The product was collected by filtration and dried under vacuum, and 76 mg of product was obtained.

4-dedimethylamino-doxycycline

To a stirred solution of tetracycline methiodide (860 mg) in 12 mL of acetic acid and 12 mL of water were added 432 mg of zinc dust. After stirring for 15 min the zinc powder was filtered out. The filtrate was diluted with 86 mL of water containing 0.86 mL of concentrated hydrochloric acid. The product that separated was filtered out and dried under vacuum, and 419 mg of product was obtained.

4-dedimethylamino-9-nitro-doxycycline

To a stirred solution of 4-dedimethylamino-doxycycline (402 mg, 1 mmol) in 20 mL of concentrated sulfuric acid at 0° C. was added 111 mg of potassium nitrate. After stirring for 20 minutes, the reaction mixture was poured into 100 mL of cold water. n-Butanol was added to the water containing the product and the organic layer was separated. Extraction with n-butanol was repeated twice. The combined organic extracts were concentrated and added to cold water with stirring. The product that separated was filtered out; more product was recovered by re-extracting the aqueous filtrate with n-butanol, concentrating, pouring into cold water and filtering. After drying under vacuum, 353 mg of product were obtained.

4-dedimethylamino-9-amino-doxycycline

To a stirred solution of 4-dedimethylamino-9-nitro-doxycycline (353 mg) in 17 mL of ethylene glycol monomethyl ether were added 0.1 mL of concentrated sulfuric acid and 200 mg of 10% Pd/C, and the resulting mixture was hydrogenated at atmospheric pressure for 10 hours. The catalyst was filtered through celite, washing with methanol. The filtrate was concentrated and poured into 100 mL of ether. The solid that separated was filtered out and dried under vacuum, and 292 mg of product was obtained.

4-dedimethylamino-9-diazonium-doxycycline hydrochloride

To a stirred solution of 4-dedimethylamino-9-amino-doxycycline (220 mg) in 5 mL of 0.1N hydrochloric acid in methanol cooled in an ice bath was added 0.2 mL of n-butyl nitrite. The solution was stirred at 0° C. for 30 minutes, then poured into 150 mL of a 2:1 cold mixture of ether/PET ether with stirring. The solid that separated was filtered out and dried under vacuum, and 191 mg of product was obtained.

4-dedimethylamino-9-azido-doxycycline

To a stirred solution of 4-dedimethylamino-9-diazonium-doxycycline (150 mg, 0.32 mmol) in 6.5 mL of 0.1N hydrochloric acid in methanol cooled in an ice bath were added 23 mg of sodium azide, and the resulting mixture was stirred for 1 hour at 0° C. The mixture was then poured into 120 mL of cold ether with stirring. Some solid formed, which was filtered out and found not to be the expected product. The filtrate was concentrated to dryness, taken up in methanol and poured into 50 mL of cold water with stirring. The solid that separated was filtered out and dried under vacuum; more product was obtained by extracting the filtrate with n-butanol, concentrating, pouring into water and filtering out the solid, and 84 mg of product was obtained.

4-dedimethylamino-7-nitro-9-tert-butyl-doxycycline

A solution of 4-dedimethylamino-doxycycline (500 mg 1.25 mmol) in 3 mL of tert-butanol and 15 mL of methanesulfonic acid was stirred at room temperature for 15 hours, then 140 mg of potassium nitrate was added and the resulting mixture stirred for an additional hour. The reaction mixture was poured in 200 ml of cold water with stirring. The solid that separated was filtered out and air dried. The crude product was dissolved in the minimum amount of methanol and purified by HPLC. The combined fractions from HPLC were concentrated to dryness, dissolved in methanol and added dropwise to 50 mL of cold water. The solid that separated was filtered out and dried under vacuum, and 217 mg of product was obtained.

4-dedimethylamino-7-amino-9-tert-butyl-doxycycline

To a stirred solution of 4-dedimethylamino-7-nitro-9-tert-butyl-doxycycline (217 mg, 0.42 mmol) in 12 mL of ethylene glycol monomethyl ether were added 170 mg of 10% Pd/C, and the resulting mixture was hydrogenated at atmospheric pressure for 13 hours. The catalyst was filtered through celite, washing with methanol. The filtrate was concentrated and poured into 20 of a 3:1 mixture of ether/PET ether, and 40 mg of product was obtained. The orange filtrate was concentrated to dryness to obtain additional 138 mg of product.

4-dedimethylamino-7-diazonium-9-tert-butyl-doxycycline

To a stirred 4-dedimethylamino-7-amino-9-tert-butyl-doxycycline (165 mg) in 5 mL of 0.1N hydrocholirc acid in methanol cooled in an ice bath was added 0.15 mL of n-butyl nitrite. The solution was stirred at 0° C. for 30 minutes; half of the material was poured into 50 mL of cold ether with stirring. The solid that separated was filtered out and dried under vacuum, and 50 mg of product was obtained.

4-dedimethylamino-7-amino-doxycycline

To a stirred solution of 4-dedimethylamino-doxycycline (400 mg) in 4 mL of THF and 4.5 mL of methanesulfonic acid at 0° C. were added 418 mg (1.4 mmol) of dibenzyl azodicarboxylate, and the resulting mixture was stirred for 4 hours while warming to room temperature. Water and n-butanol were added and two layers separated. The aqueous layer was extracted with a mixture of ether/n-butanol. The combined organic extracts were concentrated to dryness, and 10 mL of ethylene glycol monomethyl ether were added. Then, 430 mg of 10% Pd/C were added and the resulting mixture hydrogenated at atmospheric pressure for 12 hours. The catalyst was filtered off through celite, washing with methanol. The filtrate was concentrated and poured into a 3:1 cold mixture of ether/PET ether with stirring; the product that separated was filtered out and dried under vacuum, and 114 mg of product was obtained.

9-nitro-minocycline sulfate

To a stirred solution of minocycline hydrochloride (1 g, 2.02 mmol) in 30 mL of concentrated sulfuric acid at 0° C. was added potassiumnitrate (246 mg). The resulting mixture was stirred for 45 minutes at 0° C., then poured into 1.2 L cold ether with stirring. The solid that separated was filtered out, washed with cold ether and dried under vacuum, and 1.33 g of product was obtained.

9-amino-minocycline sulfate

To a stirred solution of 9-nitro-minocycline sulfate (500 g, 0.83 mmol) in 10 mL of ethylene glycol monomethyl ether and 7 mL of methanol were added 250 mg of 10% Pd/C. The reaction mixture was hydrogenated at atmospheric pressure for 4 hours. The catalyst was filtered off through celite, washing with methanol. The filtrate was concentrated, then added dropwise to 600 mL cold ether with stirring. The solid that separated was filtered out, washed with cold ether and dried under vacuum, and 465 mg of product was obtained.

9-diazonium-minocycline sulfate hydrochloride

To a stirred solution of 9-amino-minocycline sulfate (100 mg) in 3 mL of 0.1N hydrochloric acid in methanol cooled in an ice bath was added 0.1 mL of tert-butyl nitrite (or n-butyl nitrite). The solution was stirred at 0° C. for 30 minutes, then poured into 100 mL of cold ether with stirring. The solid that separated was filtered out and dried under vacuum, and 87 mg of an orange-brown product was obtained.

9-azido-minocycline sulfate

To a stirred solution of 9-diazonium-minocycline sulfate hydrochloride (485 mg, 0.83 mmol) in 18 mL of 0.1N hydrochloric acid in methanol were added 59 mg of sodium azide. The solution was stirred at room temperature for 2 hours, then filtered, and the filtrate was poured into 500 mL of cold ether with stirring. The solid that separated was filtered out and dried under vacuum, and 480 mg of beige product was obtained.

9-acetamido-minocycline

To a stirred solution of 9-amino-minocycline sulfate (100 mg, 0.175 mmol) in 1.5 mL of 1,3-dimethyl-2-imidazolidinone were added 100 mg of sodium bicarbonate followed by 0.05 mL of acetyl chloride. The mixture was stirred at room temperature for 45 minutes and then poured into 150 mL of cold ether with stirring. The solid that separated was filtered out and dried under vacuum, and 165 mg of product was obtained.

4-dedimethylamino-minocycline

Minocycline free base (175 mg, 0.38 mmol) was dissolved in 2 mL of THF, then 0.43 mL of methyl iodide was added. No crystallization of the product occurred. The reaction mixture was concentrated and poured into 200 mL of cold ether/PET ether 40:60 with stirring. The product that separated was filtered out and dried under vacuum; the product was resubjected to the reaction conditions for 3 additional days, then precipitated from ether as before, and 123 mg of minocycline methiodide was obtained. The crude product was dissolved in 2 mL of acetic acid, and 2 mL of water and 60 mg of zinc dust were added with stirring. After 15 minutes, the zinc powder was filtered out. The filtrate was diluted with 15 mL of water containing concentrated hydrochloric acid. The combined organic extracts were dried over magnesium sulfate and concentrated. The solid that separated was filtered out and dried under vacuum, and 150 mg of a yellow product was obtained.

4-dedimethylamino-9-nitro-minocycline

4-Dedimethylamino minocycline (415 mg, 1 mmol) was dissolved in 30 mL of concentrated sulfuric acid at room temperature. The solution was cooled on an ice bath and potassium nitrate (110 mg, 1.09 mmol) was added with stirring. The resulting mixture was stirred for 15 minutes, then poured into 300 mL cold ether with stirring. The solid that separated was filtered out, washed with cold ether and dried under vacuum. LC/MS showed incomplete conversion of starting material so the product was redissolved in 15 mL of concentrated sulfuric acid, 50 mg of potassium nitrate were added at 0° C. and the resulting mixture was stirred for 45 minutes. The product was isolated as before, and 542 mg of product was obtained.

7,9-dibromo sancycline

To a stirred solution of sancycline (50 mg, 0.12 mmol) in 1.5 mL of concentrated sulfuric acid at 0° C. were added 42 mg of N-bromosuccinimide. After 30 minutes, the reaction mixture was poured into 60 mL of cold ether with stirring. The solid that separated was filtered out and dried under vacuum, and 70 mg of yellow product was obtained.

Mix of 7-nitro and 9-nitro-sancycline

To a stirred solution of sancycline (40 mg, 0.09 mmol) in 1.5 mL of concentrated sulfuric acid at 0° C. was added 10 mg of potassium nitrate. After 20 minutes, the reaction mixture was poured into 50 mL of cold ether with stirring. The solid that separated was filtered out and dried under vacuum, and 59 mg of product was obtained. LC/MS shows a 1.6:1 ratio of two mono-nitrated products.

In further testing of the present invention, the Minimum Inhibitory Concentrations (MIC) of five test products when challenged with ten different microorganism strains were evaluated. The study was an MIC evaluation for five test products, performed using a modification of the Macrodilution Broth Method outlined in NCCLS document M7-A5, *Methods for Dilution Antimicrobial Susceptibility Tests for Bacteria that Grow Aerobically*, Fifth Edition. Each test product was evaluated, in duplicate, against challenge suspensions of ten microorganism strains. Prior to using each product for testing, it was diluted (w/v) in sterile Mueller-Hinton Broth (MHB) to achieve an initial concentration, based on a potency of 1000 µg/mg, of 160 µg/mL.

| | |
|---|---|
| Product 1 - Tetracycline Derivative Lot Number: INN01182 (MW 615) | 14.8 mg of this product was dissolved in 92.5 mL of MHB to achieve the initial concentration of 160 µg/mL |
| Product 2 - Tetracycline Derivative Lot Number: INN01183 (MW 627) | 13.6 mg of this product was dissolved in 85.0 mL of MHB to achieve the initial concentration of 160 µg/mL |
| Product 3 - Tetracycline Derivative Lot Number: INN01185 (MW 655) | 11.9 mg of this product was dissolved in 74.4 mL of MHB to achieve the initial concentration of 160 µg/mL |
| Product 4 - Tetracycline Derivative Lot Number: INN01189 (MW 625) | 9.6 mg of this product was dissolved in 60.0 mL of MHB to achieve the initial concentration of 160 µg/mL |
| Product 5 - Tetracycline Derivative Lot Number: INN01195 (MW 643) | 13.8 mg of this product was dissolved in 86.25 mL of MHB to achieve the initial concentrations of 160 µg/mL |

Approximately 48 hours prior to testing, separate sterile tubes of Tryptic Soy Broth were inoculated from lyophilized vials containing each of the challenge microorganisms, as found in Table I, below. The broth cultures were incubated at 35°±2° C. for approximately 24 hours. The broth cultures prepared as described above were inoculated onto the surface of Tryptic Soy Agar contained in Petri plates, and incubated at 35°±2° C. for approximately 24 hours. This produced "lawns" of the microorganisms on the surface of the agar plates, which were used to prepare the challenge suspensions.

Prior to initiating testing, an initial challenge suspension containing approximately $1.0 \times 10^9$ CFU/mL was prepared for each microorganism by inoculating a test tube of Sodium Chloride Irrigation with microorganisms taken from the plates of solid media, prepared as described above. The final challenge suspensions containing approximately $1.0 \times 10^6$ CFU/mL were prepared for each microorganism species, by placing a 0.2 mL aliquot of the $1.0 \times 10^9$ CFU/mL suspension into a sterile 250 mL polypropylene bottle, containing 200 mL of Mueller-Hinton Broth. The final challenge suspensions were mixed thoroughly prior to use in testing. The final plated dilutions were $10^{-3}$, $10^{-4}$ and $10^{-5}$. These plates were incubated at 35°±2° C. until sufficient growth was observed (Table I).

Following incubation, the colonies on the plates were counted manually using a hand-tally counter. Counts in the 30 to 300 CFU range were used in the data calculations. The Initial Population (CFU/mL) was calculated for each challenge suspension as follows:

$$CFU/mL = (C_i \times 10^{-D})$$

Where:
$C_i$=Average of the 2 Plates Counted
D=Dilution Factor of the Plate Counts Used The population (CFU/mL) per tube of product/broth following inoculation was calculated for each challenge suspension as follows:

$$\text{Population per Tube }(CFU/mL) = \frac{(C_i \times 10^{-D})}{2}$$

Where:
$C_i$=Average of the Two (2) Plates Counted
D=Dilution Factor of the Plate Counts Used
2=Total Volume (mL) present in each product/broth tube following inoculation The testing procedure was as follows: 30 mL aliquots of Mueller-Hinton Broth were dispensed into sterile bottles. A 30 mL aliquot of product (initial concentration of 160 μg/mL) was dispensed into the first of a series of 11 sterile bottles, each containing 30 mL of Mueller-Hinton Broth, and mixed thoroughly in order to achieve the 1:2 (v/v) dilution of product. A 30 mL aliquot was removed from the bottle prepared as described above, and used to initiate a 1:2 (v/v) dilution series through the remaining 10 bottles (1:4, 1:8, 1:16, 1:32, 1:64, 1:128, 1:256, 1:512, 1:1,024 and 1:2,048 product dilutions), each containing 30 mL of Mueller-Hinton Broth. Each bottle was mixed thoroughly prior to removing the 30 mL aliquot required for the next dilution in the series. 1.0 mL aliquots of each product dilution prepared and 1.0 mL aliquots of the initial product preparation (160 μg/mL product concentration) were transferred to separate sterile test tubes. A series of 12 tubes, each containing 1.0 mL of the appropriate product dilution (1:1, 1:2, 1:4, 1:8, 1:16, 1:32, 1:64, 1:128, 1:256, 1:512, 1:1,024, and 1:2,048) was prepared for each microorganism evaluated against each product (Table I). This resulted in product concentrations ranging from 160 μg/mL to 0.078 μg/mL.

A 1.0 mL aliquot of a suspension containing approximately $1.0 \times 10^6$ CFU/mL was introduced into each product dilution tube in the series, thereby resulting in a final product dilution series of 1:2, 1:4, 1:8, 1:16, 1:32, 1:64, 1:128, 1:256, 1:512, 1:1,024, 1:2,048, and 1:4,096, with each dilution tube containing approximately $5.0 \times 10^5$ CFU/mL of the challenge microorganism. This resulted in final product concentrations ranging from 80 μg/mL to 0.039 μg/mL. The test procedure described above was performed, in duplicate, for each microorganism species tested (Table I) against each test product. A positive control tube (growth control) containing a 1.0 mL aliquot of Mueller-Hinton Broth and a 1.0 mL aliquot of the challenge suspension was prepared for each microorganism (Table I). A negative (media) control tube (sterility control; no microbial inoculation) of Mueller-Hinton Broth was also prepared.

Product turbidity controls were prepared for each product by transferring 1.0 mL aliquots of each product dilution into separate sterile test tubes. A 1.0 mL aliquot of sterile Mueller-Hinton Broth was introduced into each product dilution tube created and mixed thoroughly using a vortex mixer, thereby resulting in a final product dilution series identical to that described above. The challenge suspension/product dilution tubes and the controls were incubated at 35°±2° C. for 20 hours, until good growth was apparent in the positive control tubes.

Following incubation, the tubes were examined for growth of the microorganisms, determined visually on the basis of turbidity.

The Minimum Inhibitory Concentration (MIC) for each test product versus each challenge microorganism was recorded as the highest dilution of test product that completely inhibited growth of the microorganism, as detected by the unaided eye. The results of the duplicate runs for each test product versus each microorganism were recorded and then averaged together to provide the final reported values.

TABLE I

| Microorganism Species | ATCC # | Incubation Time* (MIC Tubes) | Incubation Temp.* | Media |
| --- | --- | --- | --- | --- |
| Enterococcus faecalis | 29212 | 20 Hours | 35° ± 2° C. | TSB/TSA/MHB |
| Escherichia coli | 25922 | 20 Hours | 35° ± 2° C. | TSB/TSA/MHB |
| Escherichia coli (Tetracycline-Resistant) | 51657 | 20 Hours | 35° ± 2° C. | TSB/TSA/MHB |
| Escherichia coli (Tetracycline-Resistant) | 51658 | 20 Hours | 35° ± 2° C. | TSB/TSA/MHB |
| Escherichia coli (Tetracycline-Resistant) | 51659 | 20 Hours | 35° ± 2° C. | TSB/TSA/MHB |

TABLE I-continued

| Microorganism Species | ATCC # | Incubation Time* (MIC Tubes) | Incubation Temp.* | Media |
|---|---|---|---|---|
| *Staphylococcus aureus* (Tetracycline-Resistant) | 27217 | 20 Hours | 35° ± 2° C. | TSB/TSA/MHB |
| *Staphylococcus aureus* (Tetracycline-Resistant) | 27659 | 20 Hours | 35° ± 2° C. | TSB/TSA/MHB |
| *Staphylococcus aureus* (Tetracycline-Resistant) | 27660 | 20 Hours | 35° ± 2° C. | TSB/TSA/MHB |
| *Staphylococcus aureus* | 29213 | 20 Hours | 35° ± 2° C. | TSB/TSA/MHB |

* = Initial Population plates were inadvertently incubated at room temperature (20°–27° C.) for approximately 48 hours prior to being incubated at 35° ± 2° C. for approximately 72 hours.

Table II presents the Minimum Inhibitory Concentrations, expressed as product dilution, for each test product versus each of the 10 microorganisms tested. Table III presents the Minimum Inhibitory Concentrations, expressed as product concentration μg/mL), for each test product versus each of the 10 microorganisms tested. The initial solution prepared for each product had a concentration, based on a potency of 1000 μg/mg, of 160 μg/mL.

In additional studies, the activity of the tetracycline derivatives of the present invention as inhibitors of matrix degrading metalloproteinases (MMPs) that are involved in malignant tumor growth and metastasis were investigated. The studies used the Dunning MAT LyLu tumor model which was developed in Copenhagen rats from a transplantable tumor, transferred from an original prostate tumor from the dorsal prostate of an aged Copenhagen male rat. The

TABLE II

| | | Minimum Inhibitory Concentrations (Expressed as Product Dilution) | | | | |
|---|---|---|---|---|---|---|
| Microorganism Species | ATCC # | Product #1 | Product #2 | Product #3 | Product #4 | Product #5 |
| *Enterococcus faecalis* | 29212 | <1:2 | 1:16 | 1:16 | 1:2 | 1:8 |
| *Escherichia coli* | 25922 | 1:2 | <1:2 | <1:2 | <1:2 | 1:2 |
| *Escherichia coli* (Tetracycline-Resistant) | 51657 | <1:2 | <1:2 | <1:2 | <1:2 | <1:2 |
| *Escherichia coli* (Tetracycline-Resistant) | 51658 | <1:2 | <1:2 | <1:2 | <1:2 | <1:2 |
| *Escherichia coli* (Tetracycline-Resistant) | 51659 | <1:2 | <1:2 | <1:2 | <1:2 | <1:2 |
| *Pseudomonas aeruginosa* | 27853 | <1:2 | <1:2 | <1:2 | <1:2 | <1:2 |
| *Staphylococcus aureus* (Tetracycline-Resistant) | 27217 | <1:2 | 1:32 | 1:32 | 1:8 | 1:16 |
| *Staphylococcus aureus* (Tetracycline-Resistant) | 27659 | <1:2 | 1:32 | 1:24 | 1:8 | 1:16 |
| *Staphylococcus aureus* (Tetracycline-Resistant) | 27660 | <1:2 | 1:32 | 1:16 | 1:8 | 1:32 |
| *Staphylococcus aureus* | 29213 | 1:8 | 1:32 | 1:32 | 1:8 | 1:32 |

TABLE III

| | | Minimum Inhibitory Concentrations (Expressed as Product Dilution) | | | | |
|---|---|---|---|---|---|---|
| Microorganism Species | ATCC # | Product #1 | Product #2 | Product #3 | Product #4 | Product #5 |
| *Enterococcus faecalis* | 29212 | >80 | 10 | 10 | 80 | 20 |
| *Escherichia coli* | 25922 | 80 | >80 | >80 | >80 | 80 |
| *Escherichia coli* (Tetracycline-Resistant) | 51657 | >80 | >80 | >80 | >80 | >80 |
| *Escherichia coli* (Tetracycline-Resistant) | 51658 | >80 | >80 | >80 | >80 | >80 |
| *Escherichia coli* (Tetracycline-Resistant) | 51659 | >80 | >80 | >80 | >80 | >80 |
| *Pseudomonas aeruginosa* | 27853 | >80 | >80 | >80 | >80 | >80 |
| *Staphylococcus aureus* (Tetracycline-Resistant) | 27217 | >80 | 5 | 5 | 20 | 10 |
| *Staphylococcus aureus* (Tetracycline-Resistant) | 27659 | >80 | 5 | 6.67 | 20 | 10 |
| *Staphylococcus aureus* (Tetracycline-Resistant) | 27660 | >80 | 5 | 10 | 20 | 5 |
| *Staphylococcus aureus* | 29213 | 20 | 5 | 5 | 20 | 5 |

MAT LyLu tumor is spontaneously metastatic to lymph nodes and lungs when injected, and produces bone metastases in approximately 80–100% of the recipient animals. Fresh dosing solutions containing 10 mg/ml of each test article in 2% carboxymethylcellulose were prepared daily and used in the testing.

The studies initially evaluated toxicity in two groups of five non-tumor bearing animals, each receiving the two tetracycline analogs (9-amino-doxycycline and 9-nitro-doxycycline) at a dose of 40 mg/kg daily for seven days.

Three groups of animals (10/group) were dosed by gavage with either vehicle, or one of the two analogs daily for three weeks, and then three times per week until death or sacrifice. Dosing was begun seven days prior to implantation of the MAT LyLu tumor cells by tail vein injection. Approximately 0.1 ml of tumor cell suspension was injected into one of the lateral tail veins. The dose to be chosen was based on two factors: (1) efficacy and (2) morbidity associated with the analog, if any. The following table (Table IV below), demonstrates survival time and weekly body weight of animals in control and treated groups. As shown in the table, 9-amino-doxycycline and 9-nitro-doxycycline demonstrated a marked increase in surviving number after tumor implantation, while also resulting in indistinguishable body weight changes as compared to the control group. This latter finding is particularly significant, in that conventional anti-cancer treatments often result in significant weight loss.

TABLE IV

| Number of Days Post Tumor Implantation | Surviving Number | | |
| --- | --- | --- | --- |
| | 9-amino-doxycycline | 9-nitro-doxycycline | Control |
| 14 | 10 | 8 | 9 |
| 17 | 10 | 8 | 8 |
| 24 | 10 | 8 | 7 |
| 27 | 10 | 8 | 6 |
| 28 | 9 | 8 | 6 |
| 29 | 9 | 6 | 5 |
| 30 | 7 | 4 | 5 |
| 34 | 7 | 4 | 3 |
| 42 | 7 | 4 | 3 |

In further studies, the inhibitory activity of MMPs, as well as percent inhibition of various cancers by various tetracycline derivative were evaluated. Results appear in Table V, below, and demonstrate the efficacy of the treatments of the present invention. One objective of the studies was to assess a series of tetracycline derivatives as inhibitors of purified human matrix metalloproteinases including MMP1, 2, 3, 7, 9 and 14. The tetracycline derivatives were effective inhibitors in the mM-µM range.

Experimental Protocols

1. Protocol for Measuring MMP1 (Collagenase-1) Inhibition by Tetracycline Derivatives MMP1 activity was determined by the release of soluble $^{14}C$ labelled collagen fragments from $^{14}C$ acetylated rat skin type I collagen (Methods in Enzymology 80 711, 1981).

Assay constituents:
100 µg $^{14}C$ labelled rat skin type I collagen (5–6000 dpm)
50 mM Tris HCl pH 7.9
15 mM $CaCl_2$ 0.02% azide
Human recombinant MMP1 3–4 nM
±Tetracycline (up to 1 mM) in a total volume of 300 µl.

Incubations were at 35° C. for 5 hours. Uncleaved collagen fibrils (which form within the first 10 minutes) were removed by centrifugation at 10,000 g, 4° C., 10 minutes. 200 µl supernatant were counted in Packard Opti Phase Supermix scintillation fluid using a scintillation counter. Only data derived from within the linear part of the assay (10–70% lysis of the collagen) were utilized. Based on percentage inhibition of the activity of MMP1 alone by a range of concentrations of each sample, the IC50 value for each tetracycline was calculated by linear regression analysis.

2. Protocol for Measuring MMP2 (Gelatinase A) Inhibition

MMP2 activity was determined by the release of trichloracetic acid, TCA, soluble fragments from $^{14}C$ acetylated rat skin type I gelatin (Methods in Enzymology 248, 470, 1995. Biochem. J. 195, 1981)

Assay constituents:
100 µg $^{14}C$ labelled gelatin (type I collagen denatured 60° C. 20 min)
50 mM Tris HCl pH 7.9
15 mM $CaCl_2$, 0.02% azide
Human recombinant MMP1, 0.1–0.5 nM
±Tetracycline (up to 1 MM) in a total volume of 250 µl.

Incubations were set at 37° C. for 16 hours. The reaction was stopped by cooling the incubations and addition of 50 µl cold 90% (w/v) trichloracetic acid with careful mixing. TCA precipitation was allowed to proceed for 15 minutes at 4° C. prior to cetrifugation at 10,000 g for 10 minutes at 4° C. 200 µl of the TCA supernatant was taken for the determination of radioactive content by scintillation counting (Packard Opti Phase Supermix scintillation fluid). Only data derived from within the linear part of the assay (10–70% lysis) were utilized. The percentage inhibition of MMP2 by each tetracycline concentration was plotted to derive the IC50 value, using linear regression analysis.

3. Protocol for Measuring MMP3 (Stromelysin 1) Inhibition

MMP3 activity was determined by the release of trichloracetic acid, TCA, soluble fragments from $^{14}C$ acetylated 13 casein (Sigma) as described in Methods in Enzymology 248, 451 (1995).

Assay constituents:
100 µg $^{14}C$ casein (7000 dpm)
50 mM Tris HCl, pH 7.9
15 mM $CaCl_2$, 0.02% azide
Human recombinant MMP3, 0.25–1.0 nM
±tetracycline (up to 1 mM) in a total volume of 250 µl.

Incubations were at 37° C. for 16 hours. The reaction was stopped by the addition of 500 µl cold 18% TCA and standing on ice for 15 minutes. TCA precipitates were removed by centrifugation at 10,000 g for 10 minutes at 4° C. and 200 µl supernatant was taken for scintillation counting. Only data derived from within the linear part of the assay (10–60% lysis) were utilized. The percentage inhibition of MMP3 by each concentration of the candidate tetracycline was plotted to derive the IC50 value, using linear regression analysis.

4. Protocol for Measuring MMP7 (Matrilysin) Inhibition

MMP7 activity was determined by the release of trichloracetic acid, TCA, soluble fragments from $^{14}C$ acetylated β casein (Sigma) as described in Methods in Enzymology 248, 451 (1995).

Assay constituents:
100 μg $^{14}C$ casein (7000 dpm)
50 mM Tris HCl, pH 7.9
15 mM $CaCl_2$, 0.02% azide
Human recombinant MMP7, 1.5 nM
±tetracycline (up to 1 mM) in a total volume of 250 μl.

Incubations were at 37° C. for 16 hours. The incubation was stopped by the addition of 500 μl cold 18% TCA and standing on ice for 15 minutes. TCA precipitates were removed by centrifugation at 10,000 g for 10 minutes at 4° C., and 200 μl supernatant was taken for scintillation counting. Only data derived from within the linear part of the assay (10–60% lysis) were utilized. The percentage inhibition of MMP7 by each concentration of the candidate tetracycline were plotted to derive the IC50 value.

5. Protocol for Measuring MMP9 (Gelatinase B) Inhibition

MMP9 activity was determined by the release of trichloracetic acid, TCA soluble fragments from $^{14}C$ acetylated rat skin type I (Methods in Enzymology 248, 470, 1995. Biochem. J. 195, 1981)

Assay constituents:
100 μg $^{14}C$ labelled gelatin (collagen denatured 60° C. 20 min)
50 mM Tris HCl pH 7.9
15 mM $CaCl_2$, 0.02% azide
Human recombinant MMP9, 1.2–2 nM
±Tetracycline (up to 1 mM) in a total volume of 250 μl.

Incubations were at 37° C. for 16 hours. The incubations were stopped by cooling the incubations and addition of 50 μl cold 90% (w/v) trichloracetic acid with careful mixing. TCA precipitation was allowed to proceed for 15 minutes at 4° C. prior to centrifugation at 10,000 g for 10 minutes at 4° C. 200 μl of the TCA supernatant was taken for the determination of radioactive content by scintillation counting (Packard Opti Phase Supermix scintillation fluid). Only data derived from within the linear part of the assay (10–70% lysis) were utilized. The percentage inhibition of MMP9 by each tetracycline concentration were plotted to derive the IC50 value.

6. Protocol for Measuring MMP14 (MTI-MMP) Inhibition by Tetracycline Derivatives MMP14 activity was determined by the release of soluble $^{14}C$ labelled collagen fragments from $^{14}C$ acetylated rat skin type I collagen (Methods in Enzymology 80 711, 1981).

Assay constituents:
100 μg $^{14}C$ labelled collagen (5–6000 dpm)
50 mM Tris HCL pH 7.9
15 mM $CaCl_2$ 0.02% azide
Human recombinant MMP14 50–100 nM
±Tetracycline (up to 1 mM) in a total volume of 300 μl.

Incubations were at 35° C. for 15 hours. Uncleaved collagen fibrils (which form within the first 10 minutes) were removed by centrifugation at 10,000 g 4° C. 10 minutes 200 μl supernatant were counted in Packard Opti Phase Supermix scintillation fluid using a scintillation counter. Only data derived from within the linear part of the assay (10–70% lysis of the collagen) were utilized. Based on percentage inhibition of the activity of MMP1 alone by a range of concentrations of each sample, the IC50 value for each tetracycline was calculated.

Another objective was to analyze the effects of specific, tetracycline derived compounds on the in-vitro chemo-invasive potential of:
C8161 human melanoma cells
MDA-MB-231 human breast cancer cells
PC3 human prostate cancer cells
RPM18226 human myeloma cancer cells
Ark human myeloma cancer cells
Arp-1 human myeloma cancer cells The Membrane Invasion Culture System (MICS) in vitro chemo-invasion assay was chosen to measure changes in the invasive potential of specific human cancer cells in response to tetracycline derived compounds. Stock solutions of each compound were hydrated in water containing 2% DMSO and pH 10.0. Upon solubilization, HCl was added to the solution to establish a pH of 7.5–8.0. This solution was then wrapped in foil and kept at 4° C. during the 24 hours of assay. Fresh compound was prepared for each assay. The in vitro chemoinvasion analyses for tumor cell invasiveness are performed using the Membrane Invasion Culture System (MICS) as previously described.

The MICS system is a thermally treated plastic manifold system consisting of two matched sets of plates containing fourteen wells, 13 mm in diameter. Interposed between these plates was a polycarbonate filter containing 10 μm pores and coated with a defined matrix composed of human laminin/collagen IV/gelatin that formed a 35 μm thick barrier between the top and bottom sections of the wells in MICS. Prior to placing this barrier in place, the lower wells were filled with serum-free RPMI culture medium made 50% in conditioned medium obtained from 2-day-old cultures of human fibroblasts which had been cleared of cells and cellular debris by either centrifugation, or filtering through a 0.45 μm sterile filter. The barrier was then placed on the lower wells and fresh serum-free medium added to the upper wells after assembly of the system. Fifty thousand tumor cells were then added to the wells either in the presence of the compound, or the DMSO vehicle (the controls). Of the 12 assay wells on each manifold, 3 randomized wells acted as controls, 3 wells received 1 μg/ml of compound, 3 received 10 μg/ml and 3 received 25 μg/ml. After 24 hours, cells and media were removed from the lower wells and replaced by phosphate buffered saline plus 2 mM EDTA. This solution was used to remove all cells from the lower well, and this wash was added to the recovered cells plus medium from the same well. These samples were then collected onto a polylysine containing polycarbonate membrane containing 3 μm pores using a Dot-Blot manifold system. These collection filters were then fixed in methanol, and stained using Wright's stain (Leukostat staining kit) in situ. The filters were then mounted on microscope slides with microscope immersion oil (which reduced the light refraction from the pores) and 5 microscopic fields were counted to calculate the number of cells which invaded through the membrane over the 24 hour period. These numbers were then statistically analyzed as discussed below.

TABLE V

| | INHIBITORY ACTIVITY OF MATRIX METALLOPROTEINASES (MMPs)[1] | | | | | | | HUMAN CELL LINE EVALUATED AND PERCENT INHIBITION | | | | |
|---|---|---|---|---|---|---|---|---|---|---|---|---|
| | | | | | | | | Breast | | Melanoma | Multiple Myeloma | Prostrate |
| COMPOUND NO. | MMP-1 | MMP-2 | MMP-3 | MMP-7 | MMP-9 | MMP-14 | | MDA-MB-231 | | C8161 | RPMI-8226 | PC-3 ML |
| 1 | 267 | >700 | 258 | 815 | 43 | 86 | 7[B] 25[B] 20 | 20[B] 25[B] 15 | 5 40[B] 20 | 20 49[B] 25[B] | 35[B] 56[B] 27[B] | 20 21[B] +8[B] 1[B] +22 | 10 21[B] +10[B] +4[B] +23[B] +3 | 15 29[B] +11 7[B] 27[B] +24[B] | 2 13[B] 20 | 47[B] 24[B] 8 | 60[B] 24[B] 15 |
| 2 | 479 | 80 | 348 | >1000 | 117 | 119 | +8 | +2 | 30[B] | 22[B] | 15[B] | | | | 3 | +1 | 25[B] |
| 3 | >1000 | >1000 | 304 | >1000 | 136 | 216 | | | | | 17 35[B] | +7 +22 | +5 | 3 | +8 35 | 3 46[B] |
| 4 | 409 | 421 | 219 | 278 | 36 | 61 | 5 6 | 6 +4 | 27[B] 15 | 24[B] 27[B] | | +4 6 17 | +5 4 37[B] | +14 36 42[B] | 10 44[B] | | |
| 5 | 647 | 86 | 237 | 441 | 194 | 447 | | | | | | | | | | | |
| 6 | 394 | 135 | 241 | >1000 | 83 | 56 | +5 24 +18 +10 | +17[B] 44[B] +41[B] +5 | 18[B] 8 7 13[B] | 33[B] 21[B] 14 41[B] | 32[B] 33[B] 16 40[B] | +6 12[B] +14[B] 11 | +25[B] 10 12 3 | +5 5 +2 +2 | 21 13 0 0 | 26 32[B] 0 +4 | 41[B] 30[B] 3 0 |
| 7 | R(5) | >1000 | 300 | 335 | 64 | >1000 | | | | | | | | | | | |
| 8 | >1000 | 599 | 232 | 388 | >1000 | >1000 | | | | | | | | | | | |
| 9 | 372 | 337 | 154 | 507 | 28 | 29 | | | | | | | | | | | |
| 10 | 499 | 484 | 96 | >1000 | 41 | 53 | | | | | | | | | | | |
| 11 | 427 | >1000 | 270 | >1000 | 96 | 46 | 9 +5 | 27[B] 0 | 21 7 | 22 28[B] | 11 30[B] | 3 | 5 | 29[B] | 40[B] 9 | 50[B] 16 | 65[B] 5 |
| 12 | >1000 | >1000 | 390[2] | 503 | 270 | >1000 | 6 | 15 | 16 | 46[B] | 41[B] | | | | +3 | 0 | 36[B] |
| 13 | 126 | 48 | 206 | >1000 | 64 | 14 | 4 | 0 | +11 6 | +13 12 | +12 14 | | | | | | |
| 14 | 279 | R | >1000 | R | R | 386 | | | | | | | | | | | |
| 15 | >1000 | 234 | 738 | 716 | 402 | 768 | | | +9 | | | +11 | +13 | +12 | 8 | 23[B] | 13 |
| 16 | 452 | 215 | >1000 | 569 | 215 | 715 | | | | | | | | | | | |
| 17 | 122 | >1000 | 350 | | 110 | 98 | | | | | | | | | | | |
| 18 | 123 | 233 | 335 | | 131 | 102 | | | | | | | | | | | |
| 19 | 270 | 925 | 394 | | 98 | 90 | | | | | | | | | | | |
| 20 | 429 | 511 | 281 | | 162 | 266 | | | | | | | | | | | |
| 21 | 293 | >1000 | >1000 | | 79 | 115 | | | | | | | | | | | |
| 22 | 396 | 254 | 462 | | 341 | 459 | | | | | | | | | | | |
| 23 | >1000 | 306 | >1000 | | >1000 | >1000 | | | | | | | | | | | |
| 24 | 405 | 724 | 191 | | 127 | 160 | | | | | | | | | | | |
| 25 | 974 | 397 | 303 | | 148 | 185 | | | | | | | | | | | |
| 26 | >1000 | 413 | >1000 | | 384 | 586 | | | | | | | | | | | |
| 27 | 498 | 963 | 149 | | 101 | 92 | 15 5 +24 +7 +41[B] +13 | 35 17 +36[B] +15 7 +25[B] | 0 11 +20 +25[B] 12 +10 | +1 +38[B] 34[B] +53[B] +20 +14[B] | 73 +51[B] 40[B] 19 61[B] 1 | 24[B] 20 4 5 13 29[B] | 6 9 +3 12 13 | 42[B] 11 34[B] 62[B] 8 35[B] | 17[B] 9 7 35[B] 28[B] 8 | 35[B] 56[B] +11[B] 28[B] 50[B] 8 | 70 70 80 61 58 69 |
| 28 | >1000 | >1000 | 231 | | 125 | 49 | | | | | | | | | | | |
| 29 | 895 | 983 | 213 | | 172 | 98 | | | | | | | | | | | |
| 30 | 576 | >1000 | 938 | >1000 | >1000 | >1000 | | | | | | | | | | | |
| 31 | 621 | 258 | >1000 | 593 | 311 | 593 | | | | | | | | | | | |
| 32 | 601 | 236 | 244 | 197 | 214 | 197 | | | | | | | | | | | |

TABLE V-continued

| | INHIBITORY ACTIVITY OF MATRIX METALLOPROTEINASES (MMPs)[1] | | | | | | HUMAN CELL LINE EVALUATED AND PERCENT INHIBITION | | | | |
|---|---|---|---|---|---|---|---|---|---|---|---|
| | | | | | | | Breast | Melanoma | Multiple Myeloma | Prostrate | |
| COMPOUND NO. | MMP-1 | MMP-2 | MMP-3 | MMP-7 | MMP-9 | MMP-14 | MDA-MB-231 | | C8161 | RPMI-8226 | PC-3 ML |
| 33 | 295 | 263 | 205 | | 142 | 94 | | | | | |
| 34 | 242 | 242 | 136 | | 308 | 197 | | | | | |
| 35 | 947 | 249 | 218 | | 397 | 108 | | | | | |
| 36 | 539 | >1000 | 283 | | >1000 | 608 | | | | | |
| 37 | 279 | >1000 | 274 | | 445 | 41 | 1 | 46[B] | 20 | 69[B] | 10 | 5 | 46[B] | 11 | 26 | 36 |
| 38 | 230 | 175 | 95 | | 215 | 69 | 37[B] | 70[B] | 1 | 66[B] | 33[B] | 13 | +11 | 37[B] | 41[B] | 41 |
| 39 | 860 | 186 | 682 | | 114 | 83 | +14 | 37 | +26 | 39 | 4 | +49[B] | +8 | 38[B] | 27[B] | 52 |
| 40 | 560 | 362 | 91 | | R | 29 | +14 | 76[B] | 11 | 24 | 5 | 10 | 46[B] | 44[B] | 67[B] | 69[B] |
| 41 | 478 | 889 | 54 | | 250 | 403 | 18[B] | 20[B] | +5 | +4 | 16 | 11 | 9 | +1 | +7 | +4 |
| 42 | R | 606 | 1557 | | 405 | 428 | 9 | 2 | 8 | 6 | 7 | +6 | 14 | +4 | 4 | 4 |
| 43 | 600 | 2482 | 174 | | 319 | | +8 | | | | | | | | | |
| 44 | 1438 | 1468 | 224 | | 591 | | | | | | | | | | | |
| 45 | 384 | 2446 | 194 | | 6626 | | | | | | | | | | | |
| 46 | 194 | 3803 | 42 | | 59 | 90 | +5 | +1 | 21 | 10 | 7 | +11 | 12 | 20 | 16 | 27[B] |
| 47 | 318 | 117 | 68 | | 88 | 60 | +16[B] | 0 | +30 | +2 | 28 | 18 | 60[B] | 3 | 3 | 5 |
| 48 | 12831 | 1929 | 506 | | 424 | 354 | | | | | | | | | | |
| 49 | 372 | 1572 | 141 | | 489 | 87 | +5 | +1 | 7 | 30[B] | 11 | +2 | 15 | 4 | +5 | 6 |
| 50 | 211 | 2533 | 48 | | 34 | 40 | 0 | 2 | +2 | 1 | +14 | +8 | +13 | +14 | +17 | +10 |
| 51 | | | | | | | +18 | 25[B] | +31[B] | +122[B] | 14 | +26[B] | +2 | +4 | +13 | 4 |
| 52 | >1000 | 250 | >1000 | >1000 | 32 | 68 | 12 | 52[B] | 15 | 30 | 2 | 26[B] | 68[B] | 52[B] | 68[B] | 70[B] |
| | | | | | | | | | | | 19[B] | 33[B] | 46[B] | 31[B] | 48[B] | 63[B] |
| 53 | | | | | | 9 | 49[B] | 83[B] | +40[B] | +158[B] | 83[B] | +95[B] | 18 | 84[B] | 29[B] | 21 | 45[B] |

| | INHIBITORY ACTIVITY OF MATRIX METALLOPROTEINASES (mmPs)[1] | | | | | | CELL LINE EVALUATED AND PERCENT INHIBITION[A] | | | | | | | | |
|---|---|---|---|---|---|---|---|---|---|---|---|---|---|---|---|
| COMPOUND NO. | MMP-1 | MMP-2 | MMP-3 | MMP-7 | MMP-9 | MMP-14 | RPMI-8226 | | | ARP-1 | | | ARK | | |
| 1 | 267 | >700 | 258 | 815 | 43 | 86 | 20 | 10 | 15 | +9 | +13 | 1 | 9 | +9 | +8 |
| | | | | | | | 21[B] | 21[B] | 29[B] | | | | 13 | 8 | 17[B] |
| 2 | 479 | 80 | 348 | >1000 | 117 | 119 | +8 | +10[B] | +11 | 10 | 7 | 6 | 20[B] | 9[B] | 10 |
| | | | | | | | 1[B] | +4[B] | 7[B] | | | | | | |
| 3 | >1000 | >1000 | 304 | >1000 | 136 | 216 | +7 | +23[B] | +27[B] | +13 | +1 | +16 | +11 | +6 | +15 |
| | | | | | | | +22 | +3 | +24[B] | | | | | | |
| 5 | 647 | 86 | 237 | 441 | 194 | 447 | 6 | 4 | 36 | +25[B] | 1 | 4[B] | +7 | 22[B] | 21[B] |
| | | | | | | | 17 | 37[B] | 42[B] | | | | | | |
| 6 | 394 | 135 | 241 | <1000 | 83 | 56 | +6 | +25[B] | +5 | | NE | | 12 | 0 | 8 |
| | | | | | | | 12[B] | 10 | 5 | | | | | | |
| 9 | 372 | 337 | 154 | 507 | 28 | 98 | 21[B] | 24[B] | 28[B] | +14 | +21[B] | 7 | 17[B] | 24[B] | 20[B] |
| 10 | 499 | 484 | 96 | >1000 | 41 | 53 | 3 | 5 | 29[B] | | NE | | 6 | +7 | 1 |
| 13 | 126 | 48 | 206 | >1000 | 64 | 14 | +11 | +13 | +12 | | NE | | 2 | +7 | 1 |

For Table V:
[A] concentrations of 1, 10 and 25 ug/mL were used
[B] significant, i.e., P < 0.05
+ = increased invasiveness
NE = not evaluated
R = to be repeated (number times repeated)
[1] $IC_{50}$ in μM unless specified otherwise
2 Predicted

Key to Table V:

| Compound | Substance |
|---|---|
| 1: | 9-nitro-6-deoxy-5-hydroxytetracycline $H_2SO_4$ |
| 2: | 9-amino-6-deoxy-5-hydroxytetracycline $H_2SO_4$ |
| 3: | 9-Isopropylamino-6-deoxy-5-hydroxytetracycline $H_2SO_4$ |
| 4: | 7-Dimethylamino-6-demethyl-6-deoxy-9-nitrotetracycline $H_2SO_4$ |
| 5: | Same as 2 |
| 6: | 9-Azido-6-deoxy-5-hydroxytetracycline $H_2SO_4$ |
| 7: | 9-Amino-7-dimethylamino-6-demethyl-6-deoxytetracycline $H_2SO_4$ |
| 8: | 9-Acetamido-7-dimethylamino-6-demethyl-6-deoxytetracycline $H_2SO_4$ |
| 9: | 7-dimethylamino-6-demethyl-6-deoxytetracycline-9-diazonium $H_2SO_4$ HCL |
| 10: | 9-Azido-7-dimethylamino-6-demethyl-6-deoxytetracycline $H_2SO_4$ |
| 11: | 6-Deoxy-5-hydroxytetracycline-9-diazonium $H_2SO_4$ |
| 12: | 7-Amino-6-deoxy-5-hydroxytetracycline $H_2SO_4$ |
| 13: | 7,9-Dibromo-6-demethyl-6-deoxytetracycline $H_2SO_4$ |
| 14: | 7-Amino-6-deoxy-5-hydroxy-9-nitrotetracycline $H_2SO_4$ |
| 15: | 7-Dimethylamino-6-deoxy-5-hydroxy-tetracycline $H_2SO_4$ |
| 16: | 9-Acetamido-6-deoxy-5-hydroxytetracycline $H_2SO_4$ |
| 17: | 7-Di-n-Butylamino-6-deoxy-5-hydroxytetracycline $H_2SO_4$ |
| 18: | 7-Di-n-Hexylamino-6-deoxy-5-hydroxytetracycline $H_2SO_4$ |
| 19: | 7-Di-(3,3-dimethylbutyl)amino-6-deoxy-5-hydroxytetracycline $H_2SO_4$ |
| 20: | 7-Azido-6-deoxy-5-hydroxy-tetracycline $H_2SO_4$ |
| 21: | 6-Deoxy-5-hydroxytetracycline-7-diazonium $H_2SO_4$ |
| 22: | 7-Acetamido-9-nitro-6-deoxy-5-hydroxytetracycline $H_2SO_4$ |
| 23: | 7-Acetamido-6-deoxy-5-hydroxytetracycline $H_2SO_4$ |
| 24: | 7-Di-n-propylamino-6-deoxy-5-hydroxytetracycline $H_2SO_4$ |
| 25: | 7-Isobutylamino-6-deoxy-5-hydroxytetracycline $H_2SO_4$ |
| 26: | 7-Acetamido-9-amino-6-deoxy-5-hydroxytetracycline $H_2SO_4$ |
| 27: | 7-Isobutylmethylamino-6-deoxy-5-hydroxytetracycline $H_2SO_4$ |
| 28: | 6-Deoxy-5-acetoxy-tetracycline $H_2SO_4$ |
| 29: | 7-Acetylisobutylamino-6-deoxy-5-hydroxytetracycline $H_2SO_4$ |
| 30: | 7-Acetamido-6-deoxy-5-hydroxytetracycline-9-diazonium $H_2SO_4$ |
| 31: | 7-Dimethylamino-6-deoxy-5-hydroxytetracycline-9-diazonium $H_2SO_4$ |
| 32: | 7-Cyclobutylamino-6-deoxy-5-hydroxytetracycline $H_2SO_4$ |
| 33: | 7-Cyclobutylmethylamino-6-deoxy-5-hydroxytetracycline $H_2SO_4$ |
| 34: | 4-Dedimethylamino-6-deoxy-5-hydroxytetracycline |
| 35: | 4-Dedimethylamino-6-deoxy-5-hydroxy-9-nitrotetracycline |
| 36: | 9-animo-4-dedimethylamino-6-deoxy-5-hydroxytetracycline sulfate |
| 37: | 4-Dedimethylamino-6-deoxy-5-hydroxytetracycline-9-diazonium sulfate |
| 38: | 7-nitro-9-tertbutyl-6-deoxy-5-hydroxytetracycline $H_2SO_4$ |
| 39: | 9-tertbutyl-6-deoxy-5-hydroxytetracycline $H_2SO_4$ |
| 40: | 7-Nitro-9-tertbutyl-4-dedimethylamino-6-deoxy-5-hydroxy-tetracycline $H_2SO_4$ |
| 41: | 4-Dedimethylamino-7-dimethylamino-6-demethyl-6-deoxy-tetracycline $H_2SO_4$ |
| 42: | 7-Acetylamino-9-azido-6-deoxy-5-hydroxy-tetracycline |
| 43: | 9-tertbutyl-6-deoxy-5-hydroxytetracycline-7-diazonium $H_2SO_4$ |
| 44: | 7-Amino-9-tertbutyl-6-deoxy-5-hydroxytetracycline $H_2SO_4$ |
| 45: | 7-Azido-9-tertbutyl-6-deoxy-5-hydroxytetracycline $H_2SO_4$ |
| 46: | 6-deoxy-5-hydroxytetracycline-4-Methiodide |
| 47: | 7-(1,2-benzylcarboxyhydrazine)-6-deoxy-5-hydroxy-tetracycline HCl |
| 48: | 4-Dedimethylamino-7-amino-6-deoxy-5-hydroxyltetracycline $H_2SO_4$ |
| 49: | 7-Amino-9-tertbutyl-4-dedimethyl-6-deoxy-5-hydroxy-tetracycline-$H_2SO_4$ |
| 50: | 4-Dedimethylamino-9-tertbutyl-6-deoxy-5-hydroxytetracycline-7-diazonium $H_2SO_4$ |
| 51: | 9-(4-fluorophenyl)-6-deoxy-5-hydroxytetracycline |
| 52: | 4-Epi-7-Chlorotetracycline hydrochloride |
| 53: | 6-Demethyl-6-deoxytetracycline HCl |

While the present invention has been described with respect to particular embodiment thereof, it is apparent that numerous other forms and modifications of the invention will be obvious to those skilled in the art. The appended claims and this invention generally should be construed to cover all such obvious forms and modifications, which are within the true spirit and scope of the present invention.

What is claimed is:

1. A method for treating breast cancer, melanoma, myeloma or prostate cancer, which comprises the step of:
administering oral dosage to a subject in need of treatment for a cancer selected from the group consisting of breast cancer, melanoma, myeloma and prostate cancer an effective amount of a compound having the formula

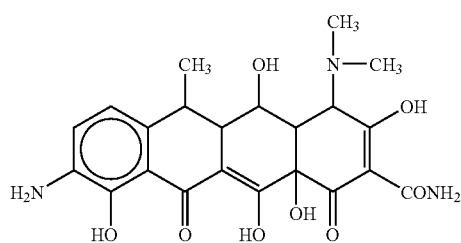

or a salt thereof.

2. A method for treating breast cancer, melanoma, myeloma or prostate cancer, which comprises the step of: administering oral dosage to a subject in need of treatment for a cancer selected from the group consisting of breast cancer, melanoma, myeloma and prostate cancer an effective amount of a compound having the formula

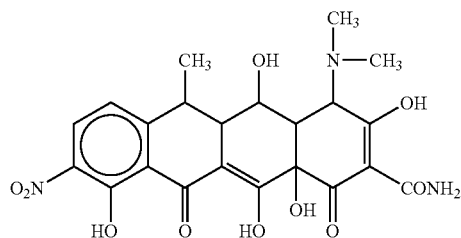

or a salt thereof.

3. The method of claim 1, wherein the step comprises administering oral dosage of 9-amino-6-deoxy-5-hydroxytetracycline $H_2SO_4$ to the subject.

4. The method of claim 2, wherein the step comprises administering oral dosage of 9-nitro-6-deoxy-5-hydroxytetracycline $H_2SO_4$ to the subject.

5. The method of claim 1, wherein the cancer is prostate cancer.

6. The method of claim 1, wherein the cancer is breast cancer.

7. The method of claim 1, wherein the cancer is melanoma.

8. The method of claim 1, wherein the cancer is myeloma.

9. The method of claim 2, wherein the cancer is prostate cancer.

10. The method of claim 2, wherein the cancer is breast cancer.

11. The method of claim 2, wherein the cancer is melanoma.

12. The method of claim 2, wherein the cancer is myeloma.

* * * * *